United States Patent
Kim et al.

(10) Patent No.: US 6,407,158 B1
(45) Date of Patent: Jun. 18, 2002

(54) WATER-SOLUBLE OR WATER-DISPERSIBLE POLYMERIC SALTS

(75) Inventors: Son Nguyen Kim, Hemsbach; Axel Sanner, Frankenthal; Peter Hössel, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/531,469

(22) Filed: Mar. 20, 2000

(30) Foreign Application Priority Data

Mar. 26, 1999 (DE) .......................... 199 13 875

(51) Int. Cl.[7] .............. C08J 3/00; C08K 3/20; C08L 51/00; C08L 67/00; C08L 75/00

(52) U.S. Cl. ............. 524/539; 424/70.1; 424/70.11; 424/70.12; 424/70.122; 424/70.16; 424/70.17; 424/70.19; 424/70.22; 424/70.21; 424/70.27; 524/588; 524/590; 524/591; 524/839; 524/840; 525/28; 525/29; 525/100; 525/101; 525/102; 525/123; 525/178; 525/179; 525/218

(58) Field of Search .................. 524/539, 588, 524/590, 591, 839, 840, 70.1, 70.11, 70.12, 70.122, 70.16, 70.17, 70.19, 70.22, 70.27, 70.21; 525/123, 28, 29, 100, 101, 102, 178, 179, 218

(56) References Cited

U.S. PATENT DOCUMENTS

| | | | |
|---|---|---|---|
| 4,192,861 A | 3/1980 | Micchelli et al. | 424/47 |
| 5,306,484 A | 4/1994 | Potthoff-Karl | 424/47 |
| 5,643,581 A | 7/1997 | Mougin et al. | 424/401 |
| 5,958,390 A | 9/1999 | Sanner et al. | 424/70 |

FOREIGN PATENT DOCUMENTS

| | | |
|---|---|---|
| DE | 4225045 | 7/1992 |
| DE | 4314305 | 4/1993 |
| DE | 19541326 | 11/1995 |
| DE | 19541658 | 11/1995 |
| EP | 619111 | 10/1994 |
| GB | 1321836 | 7/1973 |
| JP | 7127480 | 4/1968 |
| JP | 3206023 | 12/1989 |
| JP | 3206024 | 12/1989 |
| WO | 89/12438 | 12/1989 |
| WO | 94/03515 | 2/1994 |
| WO | 97/17052 | 5/1997 |
| WO | 97/17386 | 5/1997 |
| WO | 97/25021 | 7/1997 |

*Primary Examiner*—Patrick D. Niland
(74) *Attorney, Agent, or Firm*—Keil & Weinkauf

(57) ABSTRACT

The present invention relates to a water-soluble or water-dispersible polymeric salt, to a cosmetic or pharmacuetical composition which comprises at least one such polymeric salt, and to the use of the polymeric salts.

13 Claims, No Drawings

WATER-SOLUBLE OR WATER-DISPERSIBLE POLYMERIC SALTS

Water-soluble or water-dispersible polymeric salts The present invention relates to water-soluble or water-dispersible polymeric salts, to the use of these salts, and to cosmetic compositions which comprise these salts.

In cosmetics, polymers with film-forming properties are used for setting, shaping and improving the structure of the hair. These hair treatment compositions generally contain a solution of the film former in an alcohol or in a mixture of alcohol and water.

Hair-setting compositions are generally sprayed on the hair in the form of aqueous-alcoholic solutions. Following the evaporation of the solvent, the individual hairs are held in the desired shape at their points of mutual contact by the polymer which is left behind. The polymers should on the one hand be sufficiently hydrophilic that they can be washed out of the hair, yet on the other hand should be hydrophobic so that, even under conditions of high atmospheric humidity, the hair treated with the polymers retains its shape and the individual hairs do not stick to one another. In order to obtain a highly efficient hair-setting effect, moreover, it is also desirable to employ polymers which have a relatively high molecular weight and a relatively high glass transition temperature (at least 10° C.).

A further demand which is currently being placed on hair-treatment compositions is that they impart flexibility, a natural appearance and shine to the hair, for example even when the hair is by its very nature particularly strong and/or dark.

When formulating hair-setting compositions, a further consideration is that because of the environmental regulations governing the emission of volatile organic compounds (VOCs) into the atmosphere, it is necessary to reduce the content of alcohol and of propellant.

It is known to use water-soluble or dispersible polyurethanes in cosmetics. Thus, for example because of their film-forming properties and a generally low viscosity in water/ethanol, they are suitable for use in hair cosmetics, such as, for example, for the formulation of hairsprays.

DE-A-42 25 045 and WO 94/03515 describe the use of water-soluble or water-dispersible, anionic polyurethanes as hair-setting agents. These polyurethanes are constructed from a) at least one compound which contains two or more active hydrogen atoms per molecule, b) at least one diol containing an acid or salt group and c) at least one diisocyanate.

The acid groups present in these polyurethanes can be converted into the corresponding salts by neutralization with at least one base. For this purpose, low molecular weight amines, such as 2-amino-2-methylpropanol, diethylaminopropylamine and triisopropanolamine, are used.

EP-A-619 111 describes the use of polyurethanes based on organic diisocyanates, diols and 2,2-hydroxymethyl-substituted carboxylates in hair-setting compositions. At least some of the carboxylic acid groups are neutralized with an organic or inorganic base, chosen from sodium hydroxide, potassium hydroxide, 2-amino-2-methylpropanol, histidine, tris(hydroxymethyl) aminomethane and triethanolamine.

DE-A-195 41 658 describes water-soluble and water-dispersible graft polymers of a polyurethane prepolymer with terminal isocyanate groups and a protein containing free amino groups.

EP-A-636 361 describes a cosmetic composition which comprises, in a cosmetically compatible carrier, at least one pseudolatex based on a polycondensate which contains at least one polysiloxane unit and at least one polyurethane and/or polyurea unit having anionic or cationic groups. The neutralizing agents used here are mineral bases, low molecular weight amines and aminoalcohols, mineral acids and low molecular weight carboxylic acids. WO 97/25021 has a similar disclosure content. The wash-off of these film formers is unsatisfactory. In addition, because of a high siloxane content, they do not have the setting action required for a hair polymer either.

DE-A-195 41 329 and WO 97/17052 describe hair-treatment compositions comprising a hair-setting polymer which is dispersible or soluble in water or in a water/alcohol mixture, and additionally a water-soluble or -dispersible siloxane-containing salt. Hairspray formulations based on these siloxane-containing salts, a non-siloxane-containing hair-setting polymer and a silicone oil lead to films which are readily removed from the surface of the hair, e.g. by mechanical stress.

The setting action of these formulations is therefore in need of improvement.

DE-A-195 41 326 and WO 97/17386 describe water-soluble or water-dispersible polyurethanes having terminal acid groups, their preparation and their use. In this case, a polyurethane prepolymer which is dispersible or soluble in water and. has terminal isocyanate groups is reacted with an amino sulfonic acid or amino carboxylic acid, in particular taurine, aspartic acid and glutamic acid.

DE-A-197 09 277 relates to polysiloxane-containing hair-setting compositions comprising from 0.5 to 15% by weight of carboxyl-containing polymers which, in neutralized form, are water-soluble or water-dispersible. The neutralizing agents used here are alkali metal carbonates, ammonia, and amines and aminoalcohols having at most 3 carbon atoms in the longest carbon chain.

None of the abovementioned documents describes polymeric salts based on polymers having free ionogenic groups and neutralizing agents having at least two ionogenic groups complementary thereto. The polyurethanes described above lead to films which are also in need of improvement with regard to their flexibility and thus with regard to the suppleness imparted to the hair.

It is known to use copolymers based on $\alpha,\beta$-ethylenically unsaturated mono- and/or dicarboxylic acids in haircare compositions.

GB-A-1 321 836 describes hair-setting compositions based on copolymers which comprise, in copolymerized form, an unsaturated dicarboxylic acid and a vinyl or vinylidene monomer. From 5 to 20% of the carboxyl groups have been neutralized with primary $C_4$–$C_{16}$-amines. The resulting films are soft and tacky, and their setting action is in need of improvement.

DE-A-29 17 504 describes an aerosol hairspray based on a copolymer of at least one unsaturated monocarboxylic acid and at least one vinyl or vinylidene monomer. At least 7 to 100% of the carboxyl groups have been neutralized, of which, to achieve good propellant compatibility, at least half have been neutralized with a long-chain primary, secondary and/or tertiary amine having from 8 to 20 carbon atoms in the longest chain. This, too, results in soft and tacky films having a setting action which is in need of improvement.

WO 89/12438 describes a hair-setting composition based on a hair polymer having carboxyl groups, at least 40 mol % of which have been neutralized with a long-chain amine chosen from amido amines, N-ethoxylated amines and ether-amines.

The abovementioned polyacrylates containing carboxylic acid groups which have been neutralized with fatty amines or ethoxylated fatty amines lead to soft, tacky films having a drastically reduced setting action. These polymers therefore have only very limited suitability for use as hair-setting agents.

JP-A-7127480 describes a hair-treatment composition based on an amine salt solution of a copolymer which comprises, in copolymerized form, an unsaturated carboxylic acid.

JP-A-03206023 describes a polymer resin for hair-treatment compositions which comprises, in copolymerized form, a) from 6 to 35% by weight of acrylic acid, methacrylic acid, itaconic acid or a mixture thereof, b) from 15 to 50% by weight of at least one $C_{10}$–$C_{18}$-alkyl (meth) acrylate, c) from 15 to 50% by weight of at least one $C_4$–$C_8$-alkyl (meth)acrylate and d) from 0 to 25% by weight of at least one other hydrophobic vinyl monomer. The resulting copolymers are neutralized with a base, chosen from ammonia, morpholine, isopropanolamine and aminoethylpropanediol.

JP-A-03206024 describes a hair-setting polymer which is similar to that in JP-A-03206023 but which additionally comprises, in copolymerized form, from 5 to 50% by weight of an N-alkyl-substituted acrylamide. The hair-setting polymers described in these two documents have a high content of hydrophobic monomers. Their wash-off is therefore in need of improvement.

DE-A-39 01 325 and DE-A-43 14 305 describe hair-setting compositions which comprise, as film former, a copolymer based on tert-butyl (meth)acrylate and (meth) acrylic acid, where the carboxyl groups of the copolymers have been partially or completely neutralized by amines. In this case, the amines are chosen from mono-, di- or trialkanolamines, alkanediolamines or primary, secondary or tertiary alkylamines. Films based on these polyacrylates are generally hard and inflexible. DE-A-197 09 277 describes polysiloxane-containing hair-setting compositions based on carboxyl-containing polymers, polysiloxanes having primary, secondary or tertiary amino groups, and low molecular weight neutralizing agents. The use of siloxanediamines which have not been further functionalized in hair-setting compositions leads to products which are readily removed from the surface of the hair, e.g. by mechanical stress. The wash-off of these formulations is also in need of improvement.

None of the abovementioned documents describes polyacrylates having anionic groups which have a cationic component based on a di- or polyfunctional amine. The above-described polyacrylates lead to films which are also in need of improvement with regard to their flexibility and thus with regard to the suppleness imparted to the hair.

It is an object of the present invention to provide water-soluble or water-dispersible polymeric salts. These salts should be suitable as a cosmetic composition, or for use in cosmetic compositions, in particular hair-treatment compositions. They should preferably form tack-free films with good flexible properties, so that hair-treatment compositions based thereon impart elasticity to the hair.

Surprisingly, we have found that this object is achieved by water-soluble or water-dispersible polymeric salts of at least one polymer having free ionogenic groups and a neutralizing agent, comprising at least one compound having at least two ionogenic groups complementary thereto.

The present invention therefore provides a water-soluble or water-dispersible polymeric salt of:

A) at least one polymer PA) having free acid groups and a neutralizing agent which comprises at least one compound VA) having at least two free amino groups per molecule, or B) at least one polymer PB) having free amino groups and a neutralizing agent which comprises at least one di- or polyvalent inorganic acid and/or at least one compound VB) having at least two free acid groups per molecule, where the compounds VA) and VB) additionally have at least one hydrophilic group, which is chosen from other ionogenic and/or ionic groups, divalent radicals of polyethers, divalent radicals of pyrrolidone-containing polymers and combinations thereof.

For the purposes of the present invention, the terms "alkyl" and "alkylene" include straight-chain and branched alkyl and alkylene groups. Preference is given in this connection to straight-chain or branched $C_1$–$C_{40}$- and particular preference is given to $C_2$–$C_{30}$-alkyl and -alkylene groups.

$C_1$- to $C_6$-alkyl is preferably methyl, ethyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl etc.

$C_2$–$C_6$-alkylene is straight-chain and branched $C_2$–$C_6$-alkylene radicals, preferably $C_2$- to $C_4$-alkylene radicals. These preferably include ethylene, propylene, propane-1,3-diyl, butane-1,4-diyl, butane-1,3-diyl, butane-1,2-diyl, butane-2,3-diyl, 2-methylpropane-1,3-diyl, pentane-1,5-diyl, pentane-1,4-diyl, pentane-1,3-diyl, pentane-1,2-diyl, 1-methylbutane-1,4-diyl, 2-methylbutane-1,4-diyl, hexane-1,6-diyl, hexane-1,5-diyl, hexane-1,4-diyl, hexane-1,3-diyl, hexane-1,2-diyl etc.

$C_6$- to $C_{40}$-alkenyl is preferably straight-chain and branched alkenyl groups, which can be mono-, di- or poly-unsaturated. Preference is given to $C_9$- to $C_{35}$-, in particular $C_{10}$–$C_{30}$-, and specifically $C_{12}$–$C_{26}$-alkenyl groups. These include in particular hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, linolyl, linolenyl, elaeostearyl etc.

The polymeric salts according to the invention are obtainable, for example, by neutralization.

In the neutralization, a polymer PA) having free (uncharged) acid groups can be reacted with a neutralizing agent which comprises at least one compound VA) having at least two free amino groups per molecule. In the neutralization, it is also possible to react a polymer PB) having free (uncharged) amino groups with a neutralizing agent which comprises at least one compound VB) with at least two free acid groups per molecule.

The acid groups of components PA) and VB) are preferably carboxylic acid and/or sulfonic acid groups.

The amino groups of components PB) and VA) are preferably primary, secondary and/or tertiary amino groups, specifically tertiary amino groups.

The polymeric salts according to the invention are preferably at least partially crosslinked. Crosslinking takes place here via ionic bonding between ionic groups of at least two different polymer chains of the polymer PA) or PB) and at least two complementary ionic groups of a component VA) or VB). The invention therefore also provides crosslinked water-soluble or water-dispersible polymeric salts.

The polymers PA) and PB) can preferably be polymers of one polymer class, mixtures ("blends") of polymers of one polymer class and mixtures of polymers from two or more polymer classes. The polymers PA) and PB) are preferably chosen from the following classes:

polyurethanes (PA and PB)
poly(meth)acrylates (PA)
poly(meth)acrylamides (PA)
pyrrolidone-containing polymers (PA and PB)
and mixtures thereof.

If the polymers PA) and PB) are mixtures of two or more classes, then these preferably contain at least one polyurethane.

Component PA) or PB) preferably comprises at least one polyurethane which comprises, in incorporated form,
a) at least one polymer having at least two active hydrogen atoms per molecule,
b) at least one compound which has two active hydrogen atoms and at least one anionogenic and/or anionic group per molecule,
c) optionally at least one compound having a molecular weight in the range from 56 to 500, which contains two active hydrogen atoms per molecule, and
d) at least one diisocyanate.

Component a) is preferably a polymer having a number-average molecular weight in the range from about 300 to 5000, preferably from about 400 to 4000, in particular from 500 to 3000. Polymers a) which may be used are, for example, polyesterdiols, polyetherols, polysiloxanes and mixtures thereof. Polyetherols are preferably polyalkylene glycols, for example polyethylene glycols, polypropylene glycols, polytetrahydrofurans etc., copolymers of ethylene oxide and propylene oxide or block copolymers of ethylene oxide, propylene oxide and butylene oxide which contain, in copolymerized form, the alkylene oxide units in random distribution or in the form of blocks. α,ω-Diaminopolyethers which can be prepared by amination of polyalkylene oxides with ammonia are also suitable. Preference is given to using polyesterdiols or mixtures which contain them as component a).

Suitable polytetrahydrofurans a) can be prepared by cationic polymerization of tetrahydrofuran in the presence of acidic catalysts, such as, for example, sulfuric acid or fluorosulfuric acid. Such preparation processes are known to the person skilled in the art.

Preferred polyesterdiols a) have a number-average molecular weight in the range from about 400 to 5000, preferably from 500 to 3000, in particular, from 600 to 2000.

Suitable polyesterdiols are all those which are normally employed to prepare polyurethanes, especially those based on aromatic dicarboxylic acids, such as terephthalic acid, isophthalic acid, phthalic acid, Na- or K-sulfoisophthalic acid, etc., on aliphatic dicarboxylic acids, such as adipic or succinic acid, etc., and on cycloaliphatic dicarboxylic acids, such as 1,2-, 1,3- or 1,4-cyclohexanedicarboxylic acid. Particularly suitable diols are aliphatic diols, such as ethylene glycol, propylene glycol, 1,6-hexanediol, neopentyl glycol, diethylene glycol, polyethylene glycols, polypropylene glycols, 1,4-dimethylolcyclohexane.

Preference is given to polyesterdiols based on aromatic and aliphatic dicarboxylic acids and aliphatic diols, especially those in which the aromatic dicarboxylic acid accounts for from 10 to 95 mol %, in particular from 40 to 90 mol % of the overall dicarboxylic acid content (the remainder being aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-NaSO$_3$-isophthalic acid/phthalic acid/adipic acid/1,6-hexanediol, adipic acid/ethylene glycol, isophthalic acid/adipic acid/neopentyl glycol, isophthalic acid/adipic acid/ neopentyl glycol/diethylene glycol/dimethylolcyclohexane, and 5-NaSO$_3$-isophthalic acid/isophthalic acid/adipic acid/ neopentyl glycol/diethylene glycol/dimethylolcyclohexane, isophthalic acid/adipic acid, neopentylglycol/ dimethylolcyclohexane.

The polysiloxanes a) are preferably compounds of the formula VII

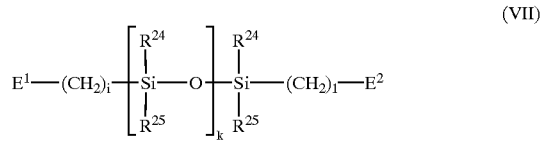

(VII)

in which
R$^{24}$ and R$^{25}$ independently of one another are C$_1$–C$_4$-alkyl, benzyl or phenyl,
E$^1$ and E$^2$ independently of one another are OH or NHR$^{26}$, where R$^{26}$ is hydrogen, C$_1$–C$_6$-alkyl or C$_5$–C$_8$-cycloalkyl,
i and l independently of one another are 2 to 8,
k is 3 to 50,
and mixtures thereof.

Suitable alkyl radicals are, for example, methyl, ethyl, n-propyl, isopropyl, n-butyl, t-butyl, n-pentyl, n-hexyl etc. Suitable cycloalkyl radicals are, for example, cyclopentyl, cyclohexyl, cycloheptyl, cyclooctyl etc.

R$^{24}$ and R$^{25}$ are preferably both methyl.

These polysiloxanes a) preferably have a number-average molecular weight in the range from about 300 to 5000, preferably from 400 to 3000.

The polysiloxanes a) are furthermore preferably compounds of the formula VIII

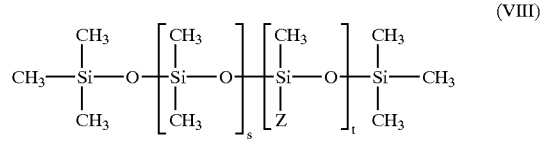

(VIII)

in which
the order of the siloxane units is arbitrary,
s is a value from 5 to 200, preferably from 10 to 100,
t is a value from 1 to 20, preferably from 2 to 10,
Z is a radical of the formula —(CH$_2$)$_u$—NH$_2$, in which u is an integer from 1 to 10, preferably from 2 to 6, or
Z is a radical of the formula —(CH$_2$)$_x$—NH—(CH$_2$)$_y$— NH$_2$, in which x and y independently of one another are from 0 to 10, preferably from 1 to 6, where the sum x+y is from 1 to 10, preferably from 2 to 6.

These include, for example, the MAN and MAR grades from Huls and the Finish grades from Wacker, for example Finish WT 1270.

Suitable compounds a) are also the polydimethylsiloxanes described in EP-A-227 816, to which reference is hereby made.

Suitable compounds b) have two active hydrogen atoms and at least one ionogenic and/or ionic group per molecule, the groups being anionogenic, anionic, cationogenic or cationic.

Preferred compounds b) having two active hydrogen atoms and at least one anionogenic and/or anionic group per molecule are, for example, compounds containing carboxylate and/or sulfonate groups. Particularly preferred components b) are 2,2-hydroxymethylalkylcarboxylic acids, such as dimethylolpropanoic acid, and mixtures which contain 2,2-hydroxymethylalkylcarboxylic acids, such as dimethylolpropanoic acid.

Suitable diamines and/or diols b) having anionogenic or anionic groups are compounds of the formula

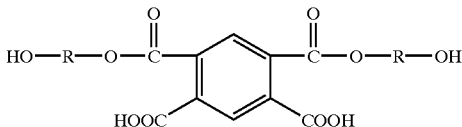

and/or

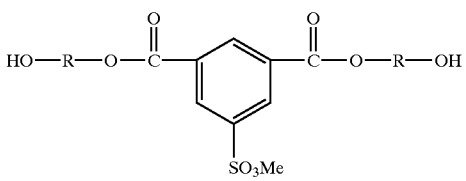

in which R is in each case a $C_2$–$C_{18}$-alkylene group, and Me is Na or K.

As component b) it is also possible to use compounds of the formula

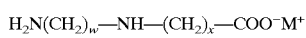

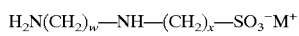

in which w and x independently of one another are an integer from 1 to 8, in particular from 1 to 6, and M is Li, Na or K, and compounds of the formula

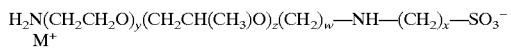

in which w and x are as defined above, y and z independently of one another are an integer from 0 to 50, where at least one of the two variables y or z is >0. The order of the alkylene oxide units is arbitrary. The last-named compounds preferably have a number-average molecular weight in the range from about 400 to 3000. A suitable compound of this type is, for example Poly ESP 520 from Raschig.

The polyurethanes can also comprise, in incorporated form, compounds b) which have two active hydrogen atoms and at least one cationogenic and/or cationic group, preferably at least one nitrogen-containing group, per molecule. The nitrogen-containing group is preferably a tertiary amino group or a quaternary ammonium group. Preference is given, for example, to compounds of the formulae

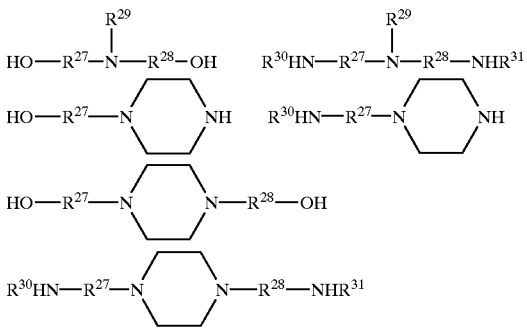

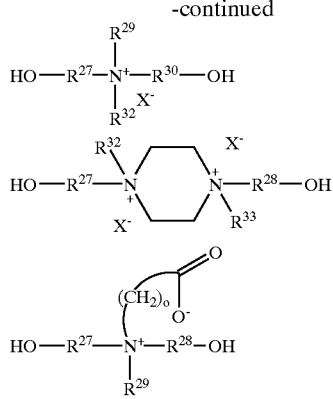

in which $R^{27}$ and $R^{28}$, which can be identical or different, are $C_2$–$C_8$-alkylene, $R^{29}$, $R^{32}$ and $R^{33}$, which can be identical or different, are $C_1$–$C_6$-alkyl, phenyl or phenyl-$C_1$–$C_4$-alkyl, $R^{30}$ and $R^{31}$, which can be identical or different, are H or $C_1$–$C_6$-alkyl, o is 1, 2 or 3, $X^{\ominus}$ is chloride, bromide, iodide, $C_1$–$C_6$-alkyl sulfate or $SO_4^{2-}/_2$.

Particular preference is given to N—($C_1$–$C_6$-alkyl) diethanolamines, such as methyldiethanolamine. These are preferably used in combination with dimethylolpropanoic acid as component b).

Also suitable as component b) are mixtures comprising two or more of the abovementioned compounds having anionic and/or anionogenic groups, two or more of the abovementioned compounds having cationic and/or cationogenic groups or mixtures which comprise at least one of the abovementioned compounds having anionic or anionogenic groups and at least one of the abovementioned compounds having cationic or cationogenic groups. Preference is given to using, for example, mixtures which comprise dimethylolpropanoic acid and N-methyldiethanolamine. In a preferred embodiment, the polyurethanes comprise predominantly or exclusively anionogenic and/or anionic groups as ionogenic and/or ionic groups. In a further preferred embodiment, the polyurethanes comprise predominantly or exclusively cationogenic and/or cationic groups as ionogenic and/or ionic groups. The polyurethanes thus preferably comprise a component b) in incorporated form which comprises predominantly, preferably in an amount of at least 80% by weight, in particular in an amount of at least 90% by weight, based on the total amount of component b), either anionogenic (anionic) compounds or cationogenic (cationic) compounds.

Component c) is preferably a diol, diamine, aminoalcohol, or a mixture thereof. The molecular weight of these compounds is preferably in a range from 56 to 300. If desired, up to 3 mol % of said compounds can be replaced by triols or triamines.

Preference is given to using diols as component c). Diols which can be used are, for example, ethylene glycol, propylene glycol, butylene glycol, neopentyl glycol, cyclohexane dimethylol, di-, tri-, tetra-, penta- or hexaethylene glycol and mixtures thereof. Preference is given to using neopentyl glycol and/or cyclohexane dimethylol.

Suitable aminoalcohols c) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc.

Suitable diamines c) are, for example, ethylenediamine, propylenediamine, 1,4-diaminobutane, 1,5-diaminopentane and 1,6-diaminohexane.

Component d) is a customary aliphatic, cycloaliphatic and/or aromatic diisocyanate, such as tetramethylene diisocyanate, hexamethylene diisocyanate, methylenediphenyl diisocyanate, 2,4- and 2,6-tolylene diisocyanate and isomer mixtures thereof, o-, m- and p-xylylene diisocyanate, 1,5-naphthylene diisocyanate, 1,4-cyclohexylene diisocyanate, dicyclohexyl methane diisocyanate and mixtures thereof, especially isophorone diisocyanate, hexamethylene diisocyanate and/or dicyclohexyl methane diisocyanate. If desired, up to 3 mol % of said compounds can be replaced by triisocyanates.

The polyurethanes are prepared by reacting the compounds of components a), b) and optionally c) and/or additional compounds having cationogenic and/or cationic groups with component d). The temperature is in a range from about 60 to 140° C., preferably from about 70 to 100° C. The reaction can be carried out without a solvent or in a suitable inert solvent or solvent mixture. Suitable solvents are aprotic polar solvents, e.g. tetrahydrofuran, ethyl acetate, N-methylpyrrolidone, dimethylformamide, and, preferably, ketones, such as acetone and methyl ethyl ketone. The reaction is preferably carried out under an inert gas atmosphere, for example under nitrogen. In addition, the reaction is preferably carried out at ambient pressure or under superatmospheric pressure. The components are preferably used in amounts such that the ratio of NCO equivalent of the compounds of component d) to equivalent of active hydrogen atom of components a), b) and optionally c) and/or other components is in a range from about 0.6:1 to 1.4:1, preferably from 0.8:1 to 1.2:1, in particular from 0.9:1 to 1.1:1. Any free isocyanate groups which may still be present in the polyurethanes can be deactivated by subsequent reaction with amines, preferably aminoalcohols. Suitable amines and aminoalcohols are those given above as component c), preferably 2-amino-2-methyl-1-propanol.

The polyurethanes preferably comprise, in copolymerized form, from 0.5 to 95% by weight, preferably from 1 to 80% by weight, of at least one component a), from 1 to 60% by weight, preferably from 3 to 40% by weight, of at least one component b), from 0 to 15% by weight, preferably from 0.3 to 12% by weight, of at least one component c), from 25 to 60% by weight, preferably from 35 to 53% by weight, of at least one component d).

If the polyurethanes described above are used according to the invention as polymer PA), then component b) comprises at least one of the above-described compounds having a free acid group. The proportion of compounds having free acid groups in component b) is then preferably at least 51% by weight, particularly preferably at least 80% by weight, in particular at least 90% by weight, based on the total amount of component b). If desired, the radical of component b) can comprise up to 100% by weight of at least one of the above-described amine-containing components.

If the polyurethanes described above are used according to the invention as polymer PB), then component b) comprises at least one of the abovementioned compounds having at least one primary, secondary or tertiary amino group. The proportion of compounds having free amino groups in component b) is then preferably at least 51% by weight, particularly preferably at least 80% by weight, in particular at least 90% by weight, based on the total amount of component b). If desired, the remainder of component b) can comprise up to 100% by weight of at least one of the above-described acid-containing components.

In a further preferred embodiment, component PA) comprises at least one polymer which comprises, in copolymerized form, e) at least one α,β-ethylenically unsaturated mono- and/or dicarboxylic acid, f) at least one α,β-ethylenically unsaturated monomer, which is chosen from esters of α,β-ethylenically unsaturated mono- and/or dicarboxylic acids with straight-chain and/or branched $C_1$–$C_6$-alkanols, amides of α,β-ethylenically unsaturated mono- and/or dicarboxylic acids with mono- and dialkylamines having straight-chain and/or branched $C_1$–$C_6$-alkyl radicals and mixtures thereof, g) optionally at least one other monomer different from e) and f) and having at least one α,β-ethylenically unsaturated double bond.

Suitable monomers e) are α,β-ethylenically unsaturated mono- and/or dicarboxylic acids and their half-esters and anhydrides, such as acrylic acid, methacrylic acid, fumaric acid, maleic acid, itaconic acid, crotonic acid, maleic anhydride, monobutyl maleate etc., and mixtures thereof. Preference is given to using acrylic acid, methacrylic acid and mixtures thereof.

Suitable monomers f) are the esters of α,β-ethylenically unsaturated mono- and dicarboxylic acids with straight-chain and/or branched $C_1$–$C_6$-alkanols, preferably $C_2$–$C_4$-alkanols, e.g. the esters of acrylic acid and/or methacrylic acid with methanol, ethanol, n-propanol, isopropanol, n-butanol, sec-butanol, tert-butanol, n-pentanol, 2-methylbutanol, n-hexanol etc.

Suitable monomers f) are also amides of α,β-ethylenically unsaturated mono- and dicarboxylic acids with mono- and dialkylamines having straight-chain and/or branched alkyl radicals, which have from 1 to 6 carbon atoms, preferably from 2 to 4 carbon atoms, per alkyl radical. These include, for example, N-$C_1$–$C_6$-alkyl(meth)acrylamides, such as N-methyl(meth)acrylamide, N-ethyl(meth)acrylamide, N-(n-propyl)(meth)acrylamide, N-isopropyl(meth) acrylamide, N-(n-butyl)(meth)acrylamide, N-(tert-butyl) (meth)acrylamide, N-(n-pentyl)(meth)acrylamide, N-(n-hexyl)(meth)acrylamide, N,N-dimethyl(meth)acrylamide, N,N-diethyl(meth)acrylamide etc.

Component f) preferably comprises at least one ester of an α,β-ethylenically unsaturated mono- and/or dicarboxylic acid with a linear $C_2$–$C_6$-alkanol. In particular, it is an ester of acrylic acid and/or methacrylic acid with ethanol, n-propanol, n-butanol, n-pentanol and n-hexanol. In particular, component f) comprises n-butyl acrylate and/or n-butyl methacrylate.

The polymers preferably.comprise, as component f) at least one linear $C_1$–$C_6$-alkyl (meth)acrylate and/or $C_1$–$C_6$-alkyl(meth)acrylamide, in particular n-butyl (meth)acrylate and/or n-butyl(meth)acrylamide, and at least one branched $C_1$–$C_6$-alkyl (meth)acrylate and/or $C_1$–$C_6$-alkyl(meth) acrylamide, in particular tert-butyl (meth)acrylate and/or tert-butyl(meth)acrylamide, in copolymerized form.

Suitable monomers g) are N-vinylamides, such as N-vinylformamide, N-vinylacetamide, N-vinylpropionamide etc. Preference is given to using N-vinylformamide.

Suitable monomers g) are also N-vinyllactams and derivatives thereof, which can have, for example, one or more $C_1$–$C_6$-alkyl substituents, such as methyl, ethyl, n-propyl, isopropyl, n-butyl, sec-butyl, tert-butyl etc. These include, for example N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc.

Suitable monomers g) are also primary amides of the abovementioned α,β-ethylenically unsaturated monocarboxylic acids, such as acrylamide, methacrylamide, ethacrylamide etc.

Suitable monomers g) are also vinyl- and allyl-substituted heteroaromatic compounds, such as 2- and 4-vinylpyridine, -allylpyridine, and preferably N-vinyl heteroaromatic compounds, such as N-vinylimidazole, N-vinyl-2-methylimidazole etc.

Suitable monomers g) are also vinyl formate, vinyl acetate, vinyl propionate, vinyl n-butyrate, vinyl stearate, vinyl laurate, styrene, a-methylstyrene, o-chlorostyrene, vinyltoluenes, vinyl chloride, vinylidene chloride, ethylene, propylene, butadiene, isoprene, chloroprene, methyl vinyl ether, ethyl vinyl ether, butyl vinyl ether, dodecyl vinyl ether etc.

Preferred monomers g) are the esters of α,β-ethylenically unsaturated mono- and dicarboxylic acids with straight-chain and/or branched $C_7$–$C_{20}$-alkanols, preferably $C_7$–$C_{12}$-alkanols, e.g. the esters of acrylic acid and/or methacrylic acid with n-heptanol, n-octanol, 2-ethyl hexanol, n-nonanol, n-decanol, n-dodecanol, etc.

Preferred monomers g) are also the amides of α,β-ethylenically unsaturated mono- and dicarboxylic acids with mono- and dialkylamines having straight-chain and/or branched alkyl radicals, which have from 7 to 20 carbon atoms, preferably from 7 to 12 carbon atoms. These include, for example, N-isopropyl (meth)acrylamide, N-(tert-butyl) (meth)acrylamide, N-ethylhexyl(meth)acrylamide, N,N-diisopropyl(meth)acrylamide etc.

The polymer PA) preferably comprises, in copolymerized form, from 1 to 60% by weight, preferably from 5 to 50% by weight, in particular from 10 to 40% by weight, of at least one component e), from 10 to 99% by weight, preferably from 20 to 95% by weight, in particular from 30 to 90% by weight, of at least one component f), from 0 to 89% by weight, preferably from 0.1 to 50% by weight, in particular from 1 to 40% by weight, of at least one component g).

In a preferred embodiment, the polymer PA) comprises, in copolymerized form, from 10 to 40% by weight, preferably from 15 to 35% by weight, of at least one component e), from 30 to 90% by weight, preferably from 35 to 80% by weight, of at least one component f), comprising at least one straight-chain $C_1$–$C_6$-alkyl (meth)acrylate and/or $C_1$–$C_6$-alkyl (meth)acrylamide having straight-chain alkyl radicals and at least one branched $C_1$–$C_6$-alkyl (meth)acrylate and/or $C_1$–$C_6$-alkyl (meth) acrylamide having branched alkyl radicals, from 0 to 60% by weight, preferably from 0.1 to 40% by weight, of at least one branched $C_1$–$C_{20}$-alkyl (meth) acrylate and/or $C_4$–$C_{20}$-mono- or dialkyl (meth) acrylamide.

These polymers PA) are prepared by customary processes known to the person skilled in the art. These include bulk polymerization and, preferably, emulsion, suspension and solution polymerization. The polymerization temperature is usually from 30 to 120° C., preferably from 40 to 100° C. The polymerization medium can, for solution polymerization, consist either only of one organic solvent or of mixtures of water and at least one water-miscible, organic solvent. Preferred organic solvents are, for example, alcohols, such as methanol, ethanol, n-propanol, isopropanol, n-butanol, ketones, such as acetone and methyl ethyl ketone, tetrahydrofuran etc. For emulsion and suspension polymerization, preference is given to using water as solvent. The polymerization can be carried out either as a batch process or in the form of a feed method, including monomer feed, stepwise and gradient procedure. Preference is generally given to the feed method in which, where appropriate, some of the polymerization mixture is heated to the polymerization temperature and then the remainder of the polymerization mixture is fed to the polymerization zone, usually via one or more spatially separate feed lines, continuously, stepwise or with superimposition of a concentration gradient with maintenance of the polymerization.

Suitable initiators for the free-radical polymerization are azo compounds which are suitable for the free-radical polymerization. These include aliphatic or cycloaliphatic azo compounds, e.g. 2,2'-azobis(isobutyronitrile), 2 2,2'-azobis(2-methylbutyronitrile), 2,2'-azobis(2,4-dimethylvaleronitrile), 1,1'-azobis(1-cyclohexanecarbonitrile), 2-(carbamoylazo)isobutyronitrile, 4,4'-azobis(4-cyanovaleric acid), and alkali metal and ammonium salts thereof, e.g. the sodium salt, dimethyl 2,2'-azobisisobutyrate, 2,2'-azobis[2-(2-imidazolin-2-yl) propane], 2,2'-azobis(2-amidinopropane) and the acid addition salts of the two last-named compounds, e.g. the dihydrochlorides.

Other suitable initiators are hydrogen peroxide, hydroperoxides in combination with reducing agents and persalts. Suitable hydroperoxides are, for example, t-butyl hydroperoxide, t-amyl hydroperoxide, cumene hydroperoxide and pinane hydroperoxide, each in combination with, for example, a salt of hydroxymethanesulfinic acid, an iron(II) salt or ascorbic acid. Suitable persalts are, in particular, alkali metal peroxydisulfates.

The amount of initiator used, based on the monomer, is generally in a range from about 0.02 to 15 mol %, preferably from 0.05 to 3 mol %.

If relatively low molecular weights are desired, these can be set by adding a regulator to the polymerization mixture. Suitable regulators are, for example, aldehydes, such as formaldehyde, acetaldehyde, propionaldehyde, n-butyraldehyde and isobutyraldehyde, formic acid, ammonium formate, hydroxylammonium sulfate and hydroxylammonium phosphate. Furthermore, it is possible to use regulators which contain sulfur in organically bonded form, such as di-n-butyl sulfide, di-n-octyl sulfide, diphenyl sulfide etc., or regulators which contain sulfur in the form of SH groups, such as n-butyl mercaptan, n-hexyl mercaptan or n-dodecyl mercaptan. Also suitable are water-soluble, sulfur-containing polymerization regulators, such as, for example, hydrogen sulfites and disulfites. Further suitable regulators are allyl compounds, such as allyl alcohol or allyl bromide, benzyl compounds, such as benzyl chloride or alkyl halides, such as chloroform or tetrachloromethane.

Suitable emulsifiers for the emulsion polymerization are the anionic, cationic and nonionic surfactants customary for this purpose and known to the person skilled in the art. If desired, the emulsion polymerization can be carried out in the presence of customary protective colloids. Suitable emulsifiers and protective colloids are, for example, described in Houben-Weyl, Methoden der Organischen Chemie, [Methods in Organic Chemistry], Vol. XIV/1, Makromolekulare Stoffe [Macromolecular Compounds], Georg-Thieme-Verlag, Stuttgart 1961, pp. 192–208 and 411–420.

If desired, one or more polymerization initiators are added to the reaction mixture following the polymerization reaction, and the polymer solution is heated, e.g. to the polymerization temperature or to temperatures above the polymerization temperature, in order to complete the polymerization. Suitable compounds are the azo initiators given above, but also all other customary initiators suitable for free-radical polymerization in aqueous solution, for example peroxides, hydroperoxides, peroxodisulfates, percarbonates, peroxo esters and hydrogen peroxide. As a result, the polymerization reaction achieves a higher conversion, such as, for example, of 99.9%. The solutions which form during the polymerization can, where appropriate, be converted into solid powders by a prior-art drying process. Preferred processes are, for example, spray drying, spray fluidized-bed drying, roller drying and belt drying. It is also possible to use freeze drying and freeze concentration. If desired, some or all of the solvent can also be removed by customary methods, e.g. by distillation at reduced pressure and, where appropriate, be replaced by the solvent used for the subsequent reaction.

Preferred polymers PA) or PB) are also pyrrolidone-containing polymers, which are obtainable, for example, by reacting a monomer mixture which comprises
h) itaconic acid and/or a derivative thereof, and
i) at least one diamine of the formula I $$H_2N—A—NHR^1 \qquad (I)$$

in which
$R^1$ is hydrogen or $C_1$–$C_4$-alkyl,
A is a $C_2$–$C_{20}$-alkylene radical, which can be interrupted by at least one or more nonadjacent, identical or different —$NR^2$— groups, where $R^2$ is hydrogen, $C_1$–$C_4$-alkyl, $C_5$–$C_8$-cycloalkyl, phenyl or phenyl-$C_1$–$C_4$-alkyl.

In a preferred embodiment, component PA) or PB) in the polymeric salts according to the invention comprises at least one pyrrolidone-containing polymer.

Preferred compounds h) are, for example, itaconic acid, itaconic anhydride, itaconic ($C_1$–$C_6$-)dialkyl esters, such as dimethyl itaconate, diethyl itaconate, itaconic acid dihalides, such as itaconic acid dichloride, etc.

Preferred compounds i) are, for example, compounds of the formula I, in which A is 1,2-ethylene, 1,3-propylene, 1,4-butylene, 2,3-butylene, pentamethylene, hexamethylene, heptamethylene, octamethylene, nonamethylene, decamethylene, —$CH_2$—O—$CH_2$—, 1,4-cyclohexylene, 1,3-cyclohexylene etc.

Preferably, in the formula I, the radical $R^1$ is hydrogen, methyl, ethyl, n-propyl, isopropyl, n-butyl or tert-butyl.

The compound i) is preferably chosen from ethylene diamine, 4,4'-biscyclohexylmethanediamine, 1,4-butylenediamine, 2,3-butylenediamine, hexamethylenediamine, 1,4-cyclohexylenediamine, 1,3-cyclohexylenediamine and mixtures thereof.

The pyrrolidone-containing polymers preferably comprise, in incorporated form, at least one further monomer k), which is chosen from amines which have two or more primary and/or secondary amino groups and additionally at least one tertiary amino group. These include, for example, the amines given above as component b) and of the formula

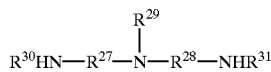

in which $R^{27}$, $R^{28}$, $R^{29}$, $R^{30}$ and $R^{31}$ are as defined above.

Preferred monomers k) are, for example, N-methyldipropylenetriamine, N-ethyldiethylenetriamine, N-methyldiethylenetriamine, N-ethyldipropylenetriamine and mixtures thereof.

The reaction of itaconic acid or its derivatives with monomeric compounds containing amino groups to give pyrrolidone structures is known in principle. The reaction is advantageously carried out under an inert gas atmosphere e.g. under nitrogen, in a solvent, preferably water, and at temperatures of from about 90 to 120° C.

The subsequent polycondensation reaction to produce polyesters and/or polyamides generally proceeds at temperatures of from 100 to 300° C., in particular from 150 to 250° C. Solvent originating from the first stage, e.g. water, is advantageously removed beforehand, for example by distillation. Water formed during the polycondensation, which is mostly produced as steam, is likewise advantageously removed, either continuously during the polycondensation or subsequently thereto. The invention is carried out at atmospheric pressure, advantageously under an inert gas atmosphere, or at increased pressure, for example up to 25 bar. The reaction is generally complete within from 2 to 10 hours.

The polycondensation reaction can be speeded up using catalysts in the amounts customary for this purpose. Suitable for this purpose are, predominantly, mineral acids or acid salts of mineral acids, e.g. orthophosphoric acid, alkali metal dihydrogenphosphates or alkali metal hydrogensulfates. Heavy metal salts of fatty acids, such as tin octanoate, can also be used for this purpose. The acidic catalysts remaining in the product can be neutralized with customary bases.

The abovementioned pyrrolidone-containing polymers can preferably be used as acid-containing polymer PA) of the polymeric salts according to the invention. To prepare pyrrolidone-containing polymers PA) having free acid groups, the components h), i) and optionally k) can be used in quantitative ratios such that the—optionally derivatized—acid groups of component h) are present in a molar excess relative to the amino groups of components i) and, if present, k). The molar excess is preferably from about 1 to 25 mol %.

Finally, derivatized acid groups can be converted into the free acid groups by hydrolysis using customary methods.

The abovementioned pyrrolidone-containing polymers can also be preferably used as amino-containing polymer PB) of the polymeric salts according to the invention. To prepare pyrrolidone-containing polymers PB) having free amino groups, the components h), i) and optionally k) can be used in quantitative ratios such that the amino groups of component i) and if present, k) are in a molar excess relative to the—optionally derivatized—acid groups of component h). The molar excess is preferably from about 1 to 25 mol %.

Suitable pyrrolidone-containing polymers and processes for their preparation are described, for example, in DE-A-43 33 238, to the entire contents of which reference is made.

In a preferred embodiment, the polymeric salts according to the invention are prepared by reacting at least one of the abovementioned polymers PA) with a neutralizing agent which has at least one compound VA) having at least two free amino groups per molecule.

Preferably, component VA) comprises at least one polyamine of the formula II

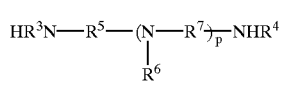

in which
p is an integer from 0 to 4,
$R^3$ and $R^4$ independently of one another are hydrogen, $C_1$- to $C_{40}$-alkyl or $C_6$- to $C_{40}$-alkenyl, where the alkyl and alkenyl radicals can carry at least one ionogenic and/or ionic group which is chosen from —COOY, —SO$_3$Y and —PO$_3$Y, where Y is H, Li, Na, K or ammonium, where, if p=0, at least one of the radicals R$^3$ or R$^4$ is a C$_1$- to C$_{40}$-alkyl or C$_6$- to C$_{40}$-alkenyl radical which carries at least one ionogenic and/or ionic group, R$^5$ and R$^7$ is C$_2$- to C$_6$-alkylene radical, where, if p is >1, the radicals R$^7$ are chosen independently from C$_2$- to C$_6$-alkylene radicals, R$^6$ is C$_1$- to C$_6$-alkyl, C$_5$- to C$_8$-cycloalkyl, phenyl or phenyl-C$_1$–C$_4$-alkyl where, if p is >1, the radicals R$^6$ are chosen independently from these meanings.

If the polyamine of the formula II has two or more repeat units ${-}(N(R^6){-}R^7{-})_{\overline{p}}$ then these can have identical or different meanings.

p is preferably 1, 2 or 3, in particular 1 or 2.

If p is 0, then the radicals R$^3$ and R$^4$ are, independently, preferably a C$_1$–C$_{40}$-alkyl or C$_6$–C$_{40}$-alkenyl radical which each carry at least one ionogenic and/or ionic group.

Preferably, R$^3$ and R$^4$ independently of one another are hydrogen, C$_1$–C$_{30}$-alkyl, preferably C$_1$–C$_{12}$-alkyl, in particular C$_1$–C$_8$-alkyl or a radical of the formula —(CH$_2$)$_{2-6}$—SO$_3$Y, where Y is H, Li, Na, K or ammonium.

In particular, R$^3$ and R$^4$ independently of one another are hydrogen, methyl, ethyl, n-propyl, isopropyl, n-butyl, sec-butyl, tert-butyl, n-pentyl, n-hexyl. Specifically, R$^3$ and R$^4$ are both hydrogen.

Preferably R$^5$ is a C$_2$–C$_4$-alkylene radical.

Preferably, R$^6$ is methyl, ethyl, n-propyl, isopropyl, n-butyl, sec-butyl, tert-butyl, cyclohexyl, phenyl or benzyl.

Preferably R$^7$ is a C$_2$–C$_4$-alkylene radical.

The polyamine of the formula II is preferably diethylenetriamine, N-methyldiethylenetriamine, N-ethyldiethylenetriamine, N,N,N',N'-tetramethyldiethylenetriamine, N,N,N',N'-tetraethyldiethylenetriamine, dipropylenetriamine, N-methyldipropylenetriamine, N-ethyldipropylenetriamine, N,N'-bis(3-aminopropyl)butane-1,4-diamine, triethylenetetramine, tetraethylenepentamine and mixtures thereof. The polyamine of the formula II is particularly preferably N-methyldipropylenetriamine.

Furthermore, the component VA) preferably comprises at least one diaminopolyether of the formula III

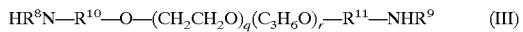

in which

R$^8$ and R$^9$ independently of one another are hydrogen, C$_1$- to C$_{40}$-alkyl or C$_6$- to C$_{40}$-alkenyl, where the alkyl and alkenyl radicals may or may not carry at least one ionogenic and/or ionic group, which is chosen from —COOY, —SO$_3$Y and —PO$_3$Y, where Y is H, Li, Na, K or ammonium, R$^{10}$ and R$^{11}$ independently of one another are a C$_2$- to C$_6$-alkylene radical, the order of the alkylene oxide units is arbitrary, and q and r independently of one another are an integer from 0 to 100, where the sum q+r is in a range from 5 to 100.

Preferably, R$^8$ and R$^9$ independently of one another are hydrogen, C$_1$–C$_{30}$-alkyl, preferably C$_1$–C$_{12}$-alkyl, in particular C$_1$–C$_8$-alkyl or a radical of the formula —(CH$_2$)$_{2-6}$—SO$_3$Y, where Y is H, Li, Na, K or ammonium.

In particular, R$^8$ and R$^9$ independently of one another are hydrogen, methyl, ethyl, n-propyl, isopropyl, n-butyl, sec-butyl, tert-butyl, n-pentyl, n-hexyl. Specifically, R$^2$ and R$^4$ are both hydrogen.

Preferably R$^{10}$ and R$^{11}$ independently of one another are a C$_2$- to C$_4$-alkylene radical, in particular a C$_2$–C$_3$-alkylene radical.

Suitable compounds of the formula III are α,ω-diaminopolyethers, which can be prepared by amination of polyalkylene oxides with ammonia. Such polyethers and preparation processes are known to the person skilled in the art. The polyethers are preferably the polyetherols mentioned above as component a) and having a number average molecular weight in the range from about 300 to 5000, preferably from about 400 to 4000.

Furthermore, component VA) preferably comprises at least one alkoxylated amine of the formula IV

in which

R$^{12}$ and R$^{13}$ independently of one another are C$_1$- to C$_{40}$-alkyl, C$_6$- to C$_{40}$-alkenyl, hydroxyalkyl or a radical of the formula —(CH$_2$CH$_2$O)$_m$(C$_3$H$_6$O)$_n$—H, where the order of the alkylene oxide units is arbitrary, and m and n independently of one another are an integer from 0 to 30, where the sum m+n is in a range from 1 to 30, R$^{14}$ and R$^{15}$ independently of one another are chosen from the meanings given for R$^{12}$ and R$^{13}$ and C$_2$- to C$_6$-alkyl radicals having an ionogenic or ionic group, which is chosen from —COOY, —SO$_3$Y adn —PO$_3$Y, where Y is H, Li, Na, K or ammonium, and R$^{16}$ is a C$_2$- to C$_6$-alkylene radical.

If, in formula IV, the radicals R$^{12}$, R$^{14}$ and, where appropriate, R$^{13}$ and/or R$^{15}$ are alkoxylate radicals, then these can each have identical or different meanings.

Preferably, for each of the alkoxylate radicals, m and n independently of one another are an integer from 0 to 20, preferably from 0 to 10, the sum m+n being in each case in a range from 1 to 20, preferably from 2 to 10.

Preferably, the alkoxylated amine of the formula IV has a total of from 1 to 50, particularly preferably from 2 to 40, in particular from 3 to 30, specifically from 3 to 20, incorporated alkylene oxide units.

Preferably, the radicals R$^{12}$ and R$^{13}$ are chosen from C$_1$–C$_{22}$-alkyl and C$_6$–C$_{22}$-alkenyl, in particular C$_8$–C$_{22}$-alkyl and C$_8$–C$_{22}$-alkenyl.

Preferably, at least one of the radicals R$^{14}$ and/or R$^{15}$ is a straight-chain or branched C$_8$–C$_{40}$-alkyl or C$_8$–C$_{40}$-alkenyl radical. Preference is given to straight-chain and branched C$_9$–C$_{35}$-, particularly preferably C$_{10}$–C$_{30}$- and specifically C$_{12}$–C$_{26}$-alkyl and -alkenyl radicals.

R$^{12}$ and/or R$^{14}$ are preferably 1-octyl, 1-nonyl, 1-decyl, 1-undecyl, 1-undec-10-enyl, 1-tridecyl, 1-tetradecyl, 1-pentadecyl, 1-hexadecyl, 1-heptadecyl, 1-octadecyl, 1-octadeca-9,12-dienyl, 1-nonadecyl, 1-eicosyl, 1-eicos-9-enyl, 1-heneicosyl, 1-docosyl and, in particular, oleyl and 1-hexadecyl (cetyl) or alkyl radicals derived from naturally occurring fatty acids by formal removal of the carboxylic acid function, the fatty acids being, for example, tallow fatty acids which largely comprise saturated and unsaturated C$_{14}$–C$_{16}$- and C$_{18}$-alkyl radicals, or coconut fats which contain saturated, mono- and diunsaturated C$_8$–C$_{22}$-, preferably C$_{12}$–C$_{14}$-alkyl fats.

In particular, one of the radicals R$^{14}$ and/or R$^{15}$ is one of the abovementioned C$_8$–C$_{40}$-alkyl- or C$_8$–C$_{40}$-alkenyl radicals and the other is one of the abovementioned alkylene oxide radicals.

Preferably, in the formula IV, the radical R$^{16}$ is a C$_2$–C$_4$-alkylene radical.

In particular, the alkoxylated amine of the formula IV is one in which

R$^{12}$, R$^{13}$ and R$^{15}$ independently of one another are hydroxyethyl or a radical of the formula —$(CH_2CH_2O)_m$—H, where m is in each case an integer from 1 to 10 and, the total number of ethylene oxide units in the radicals $R^{12}$, $R^{13}$ and $R^{15}$ is in a range from 3 to 20, preferably from 4 to 15, and $R^{14}$ is a $C_8$–$C_{20}$-alkyl or alkenyl radical.

The radical $R^{14}$ is preferably an oleyl or tallow radical.

Suitable alkoxylated amines of the formula IV are, for example, the Dinoramox® products from Ceca and, in particular, Dinoramox® S3 or S7, i.e. ethoxylated n-tallowpropylenediamines having 3 and 7 ethylene oxide units respectively. Also suitable are hydroxyethylated or ethoxylated oleyl-propylenediamines having from 3 to 7, in particular 5, ethylene oxide units.

With further preference, compound VA) is a diaminopolyether siloxane of the formula V, which is chosen from polysiloxanes having repeat units of the formula V.1

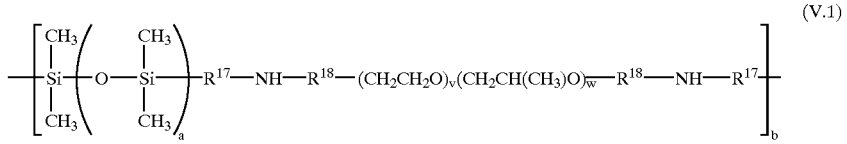
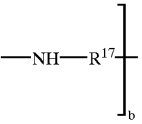

in which a is an integer from 0 to 100, b is an integer from 1 to 8, $R^{17}$ and $R^{18}$ independently of one another are $C_1$- to C8-alkylene, the order of the alkylene oxide units is arbitrary and v and w independently of one another are an integer from 0 to 200, where the sum v+w is >0, polysiloxanes of the formula V.2

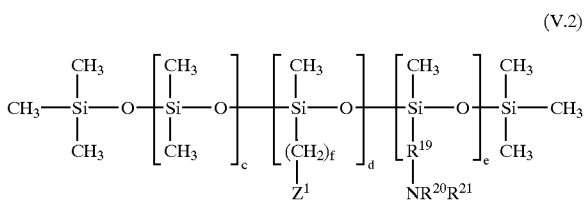

in which $R^{19}$ is a $C_1$- to $C_8$-alkylene radical, $R^{20}$ and $R^{21}$ independently of one another are hydrogen, $C_1$- to $C_8$-alkyl or $C_5$- to $C_8$-cycloalkyl, the order of the siloxane units is arbitrary, c, d and e independently of one another are 0 to 100, where the sum c+d+e is at least 3, f is an integer from 2 to 8, $Z^1$ is a radical of the formula VI

in which the order of the alkylene oxide units is arbitrary and g and h independently of one another are an integer from 0 to 200, where the sum g+h is >0, $R^{22}$ is a $C_1$- to $C_8$-alkylene radical, and $R^{23}$ is hydrogen or a $C_1$- to $C_8$-alkyl radical.

and mixtures thereof.

Preferably, in the formula V.1, $R^{17}$ and $R^{18}$ independently of one another are a $C_2$–$C_4$-alkylene radical. In particular, $R^{17}$ and $R^{18}$ independently of one another are a $C_2$–$C_3$-alkylene radical.

The molecular weight of the compound of the formula V.1 is preferably in a range from about 300 to 100,000.

In the formula V.1, a is preferably an integer from 1 to 20, such as, for example, from 2 to 10.

The total number of alkylene oxide units in the compound of the formula V.1, i.e. the sum v+w, is preferably in a range from about 3 to 200, preferably from 5 to 180.

Preference is given to the end groups of the polysiloxanes having repeat units of the formula V.1 selected from $(CH_3)_3$ SiO, H, $C_1$–$C_8$-alkyl and mixtures thereof.

Suitable alkoxylated siloxane-amines of the formula V.1 are described, for example, in WO-A-97/32917, to the entire contents of which reference is made here. Commercially available compounds are, for example, the Silsoft® products from Witco, e.g. Silsoft® A-843.

Preferably, in the formula V.2, the radical $R^{19}$ is a $C_2$–$C_4$-alkylene radical.

Preferably, in the formula V.2, $R^{20}$ and $R^{21}$ independently of one another are hydrogen or $C_1$–$C_4$-alkyl.

Preferably, the sum c+d+e is chosen such that the molecular weight of the compound of the formula V.2 is in a range from about 300 to 100,000, preferably from 500 to 50,000.

Preferably, the total amount of alkylene oxide units in the radical of the formula VI, i.e. the sum g+h, is in a range from about 3 to 200, preferably from 5 to 80.

Preferably, in the formula VI, the radical $R^{22}$ is $C_2$–$C_4$-alkyl.

Preferably, in the formula VI, the radical $R^{23}$ is hydrogen or $C_1$–$C_4$-alkyl.

A suitable compound of the formula V.2 is, for example, Silsoft® A-858 from Witco.

Furthermore, the component VA) preferably comprises at least one pyrrolidone-containing polymer having at least two free primary, secondary and/or tertiary amino groups per molecule. It is preferably a pyrrolidone-containing polymer, as described above as component PB).

The neutralizing agents which can be used for the polymers PA) are the abovementioned compounds VA) each individually or in the form of mixtures. For the neutralization of the polymers PA) it is also possible to use mixtures of two or more bases which contain at least one compound VA) and at least one other base. Suitable other bases for the neutralization of the polymers are alkali metal bases, such as sodium hydroxide solution, potassium hydroxide solution, sodium carbonate, potassium carbonate, sodium hydrogencarbonate, potassium hydrogencarbonate and alkaline earth metal bases, such as calcium hydroxide, calcium oxide, magnesium hydroxide or magnesium carbonate, and ammonia and amines which do not form a counterion B). For the neutralization of the polymers having anionogenic groups, preference is given to using mixtures which contain at least one amine of the formula I and an alkali metal hydroxide, preferably potassium hydroxide. For neutralization of the polyurethanes having anionogenic groups, preference is also given to using mixtures which contain at least one amine of the formula I and an aminoalcohol, preferably 2-amino-2-methyl-1-propanol.

If the polymer used is a polyurethane which additionally has amine groups as cationogenic groups, then, if desired, these cationogenic groups can be converted, partially or completely, into the corresponding cationic groups by neutralization with an acid or by quaternization.

In a preferred embodiment, a carboxylic acid of the formula $R^{27}$—COOH is used for the neutralization, in which $R^{27}$ is a $C_8$–$C_{40}$-alkyl radical or a $C_8$–$C_{40}$-alkenyl radical. Preference is given to using a carboxylic acid which is chosen from caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid, melissic acid, tuberculostearic acid, palmitoleic acid, oleic acid, linoleic acid, linolenic acid, elaeostearic acid and mixtures thereof. Suitable acids for the neutralization are also inorganic acids, such as phosphoric acid, and carboxylic acids, such as lactic acid, and mixtures of the abovementioned acids.

If desired, cationogenic groups can also be partially or completely quaternized. The quaternization can, for example, be carried out using alkylating agents, such as $C_1$–$C_4$-alkyl halides or sulfates. Preferred alkylating agents are ethyl chloride, ethyl bromide, methyl chloride, methyl bromide, dimethyl sulfate and diethyl sulfate.

In a further preferred embodiment, the polymeric salts according to the invention are prepared by reacting at least one of the abovementioned polymers PB) with a neutralizing agent which has at least di- or polybasic inorganic acids and/or a compound VB) having at least two free acid groups per molecule.

The compound VB) is preferably a straight-chain or branched $C_6$–$C_{40}$-di- or polycarboxylic acid. This can, if desired, have one or more additional functional groups, such as, for example, hydroxyl groups. Suitable di- and polycarboxylic acids are, for example, adipic acid, azelaic acid, dodecane dioic acid, suberic acid, pimelic acid, sebacic acid, tetradecanedioic acid, citric acid etc.

In addition, the compound VB) is preferably a pyrrolidone-containing polymer having at least two free carboxylic acid groups per molecule. It is preferably a pyrrolidone-containing polymer, as described above as component PA).

Suitable di- or polybasic inorganic acids are, for example, $H_3PO_4$ or $H_2SO_4$.

Neutralizing agents which can be used for the polymers PB) are the abovementioned compounds VB) each individually or in the form of mixtures. For the neutralization of the polymers PB), it is also possible to use mixtures of two or more acids which contain at least one compound VB) and at least one other acid. Suitable other acids for the neutralization of the polymers PB) are the carboxylic acids described above for the neutralization of cationogenic groups of polyurethanes.

The proportion of the compound VA) or VB) in the polymeric salt is preferably at least about 0.1% by weight, in particular at least 0.5% by weight.

The proportion of the compound VA) or VB) in the polymeric salt is preferably at most about 50% by weight, preferably at most about 40% by weight.

Preference is given to polymeric salts, as described above, where the ratio of

A) free acid groups in the polymer PA) to free amino groups in the compound VA), or B) free amino groups in the polymer PB) to free acid groups in the compound VB) is in a range from 1:0.005 to 1:1, preferably 1:0.01 to 1:0.5.

The reaction of the polymers PA) and PB) with the neutralizing agent can preferably be carried out immediately following the preparation of the polymers and generally in the same reaction vessel. If desired, to prepare the salts according to the invention, it is also possible to use a separately prepared or commercially available polymer. Suitable polyurethanes are described, for example, in DE-A-42 41 118, DE-A-42 25 045 and EP-A-0 619 111, to the entire contents of which reference is made. Suitable acrylate copolymers are described, for example, in DE-A-39 01 325 and DE-A-43 14 305, to the entire contents of which reference is made. Suitable pyrrolidone-containing polymers are described, for example, in DE-A-43 33 238, to the entire contents of which reference is made. Suitable solvents for the reaction are those mentioned above for the preparation of polyurethanes.

Polyurethanes which have both cationogenic and also anionogenic groups can be subjected successively to neutralization with at least one acid, neutralization with at least one base and, if desired, additionally to quaternization. The order of the neutralization step is generally arbitrary.

If, in the preparation of the polymeric salts, a water-miscible organic solvent is used, then this can be removed immediately afterwards by customary processes known to the person skilled in the art, e.g. by distillation at reduced pressure. Prior to removal of the solvent, water can additionally be added to the polymeric salt. Replacement of the solvent by water gives a solution or dispersion of the polymeric salt, from which, if desired, the polymeric salt can be obtained in the usual manner, e.g. by spray drying.

The pH of the aqueous solutions or dispersions can be adjusted by adding an acid or base. Suitable acids and bases are those given above as additional neutralizing agents. The pH for anionic polymeric salts is preferably in the alkaline range, in particular >7.5. Preferably, the pH for cationic polymeric salts is in the acidic range, in particular from 5.5 to 6.5.

The polymeric salts according to the invention are soluble in water or dispersible in water. They generally form clear and tack-free films and can be washed out very readily with water. Advantageously, the polymeric salts according to the invention also give films having a very good elasticity. This elasticity is generally higher than the elasticity which is usually obtained in the case of polyurethanes containing short-chain groups known from the prior art. Hair-treatment compositions based on these salts impart very good suppleness to the hair.

The polymeric salts according to the invention are particularly suitable as or in hair-setting polymers which impart flexibility to the hair.

The polymeric salts according to the invention can be used as auxiliaries in cosmetics, preferably as or in coating compositions for keratin-containing and keratin-analogous surfaces, such as hair, skin and nails. They are particularly suitable for hair cosmetics, preferably as setting polymers in hairsprays, setting mousses, hair mousse, hair gel and shampoos. They are also preferably suitable for use in decorative cosmetics, in particular in mascara and eyeshadows. The polymeric salts according to the invention can also be used as auxiliaries in pharmacy, preferably as or in coatings or binders for solid medicaments. The abovementioned polymeric salts can also be used in creams and as tablet coatings and tablet binders. They are also suitable as binders and adhesives for cosmetic products, e.g. in the manufacture of stick-shaped cosmetic products, such as deodorant sticks, make-up sticks etc. The polymeric salts according to the invention are also preferably suitable for use as or in coatings for the textile, paper, printing, leather and adhesives industries. The polymeric salts according to the invention which comprise, as polymer PA) or PB) and/or as compound VA) or VB), at least one pyrrolidone-containing polymer, are preferably suitable for use in skin cosmetics, preferably in creams.

The invention also provides a cosmetic or pharmaceutical composition which comprises at least one polymeric salt according to the invention. The composition generally comprises the polymeric salts in an amount in the range from about 0.2 to 30% by weight, preferably from 0.5 to 20% by weight, based on the total weight of the composition.

The cosmetic compositions according to the invention are suitable in particular as coating compositions for keratin-containing and keratin-analogous surfaces (hair, skin and nails). The compounds used therein are water-soluble or water-dispersible. If the compounds used in the compositions according to the invention are water-dispersible, they can be used in the form of aqueous microdispersions having particle diameters of customarily from 1 to 250 mm, preferably from 1 to 150 mm. The solid contents of the preparations is usually in a range from about 0.5 to 20% by weight, preferably from 1 to 12% by weight. These microdispersions do not generally require emulsifiers or surfactants for their stabilization.

Preferably, the compositions according to the invention can be in the form of a hair-treatment composition, such as setting foam, hair mousse, hair gel, shampoo and, in particular, in the form of a hairspray. For use as a hair-setting compositions, preference is here given to compositions which comprise polymeric salts which have at least one glass transition temperature Tg of $\geq 0°$ C., preferably $\geq 10°$ C. The K value of these polymers (measured in accordance with E. Fikentscher, Cellulose-Chemie 13 (1932), pp. 58–64) on a 1% strength by weight solution in N-methylpyrrolidone, is preferably in a range from 23 to 90, in particular from 25 to 60. If the salts according to the invention have siloxane groups, then the siloxane content of these polymers is generally from 0.05 to 20% by weight, based on the total weight of the incorporated components.

The compositions are preferably hair-treatment compositions. They are usually in the form of an aqueous dispersion or in the form of an alcoholic or aqueous-alcoholic solution. Examples of suitable alcohols are ethanol, propanol, isopropanol etc.

In addition, the hair-treatment compositions according to the invention can generally comprise customary cosmetic auxiliaries, for example softeners, such as glycerol and glycol; emollients; perfumes; surfactants; UV absorbers; dyes; antistats; combability improvers; preservatives; and antifoams.

If the compositions according to the invention are formulated as hairsprays, they comprise a sufficient amount of a propellant, for example a low-boiling hydrocarbon or ether, such as propane, butane, isobutane or dimethyl ether. Propellants which can be used are also compressed gases, such as nitrogen, air or carbon dioxide. The amount of propellant can be kept low so as not to raise the VOC content unnecessarily. In general, the amount is then no more than 55% by weight based on the total weight of the composition. However, higher VOC contents of 85% by weight and above are also possible if desired.

The polyurethanes described above can also be used in the compositions in combination with other hair polymers. Such polymers are, in particular:

nonionic, water-soluble or water-dispersible polymers or oligomers, such as polyvinylcaprolactam, e.g. Luviskol Plus (BASF), or polyvinylpyrrolidone and its copolymers, in particular with vinyl esters, such as vinyl acetate, e.g. Luviskol VA 37 (BASF); polyamides, e.g. those based on itaconic acid and aliphatic diamines, as described, for example, in DE-A-43 33 238;

amphoteric or zwitterionoic polymers such as the octylacrylamide/methylmethacrylate/tert-butylaminoethyl methacrylate/2-hydroxypropyl methacrylate copolymers obtainable under the names Amphomer® (National Starch), and zwitterionic polymers as disclosed, for example in German Patent applications DE 39 29 973, DE 21 50 557, DE 28 17 369 and DE 37 08 451. Acrylamidopropyltrimethylammonium chloride/acrylic acid and methacrylic acid copolymers and alkali metal and ammonium salts thereof are preferred zwitterionic polymers. Other suitable zwitterionic polymers are methacroylethylbetaine/methacrylate copolymers, which are available commercially under the name Amersette® (AMERCHOL), and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are commercially available, for example under the names Resyn® (NATIONAL STARCH), Luviset® (BASF) and Gafset® (GAF), and vinylpyrrolidone/vinylacrylate copolymers, obtainable for example under the tradename Luviflex® (BASF). A preferred polymer is the vinyl pyrrolidone/acrylate terpolymer available under the name Luviflex® VBM-35 (BASF). Acrylic acid/ethyl acrylate/N-tert-butylacrylamide terpolymers, which are marketed, for example under the name Ultrahold® strong (BASF), and Luvimer® (BASF, terpolymer of t-butyl acrylate, ethyl acrylate and methacrylic acid), sodium sulfonate-containing amides or sodium sulfonate-containing polyesters, or cationic (quaternized) polymers, e.g. cationic polyacrylate copolymers based on N-vinyl lactams and derivatives thereof (N-vinylpyrrolidone, N-vinylcaprolactam etc.) and customary cationic hair-conditioning polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers formed by reacting polyvinylpyrrolidone with quaternary ammonium compounds), polymer JR (hydroxyethylcellulose with cationic groups), polyquaternium products (CTFA names) etc.;

nonionic, siloxane-containing, water-soluble or -dispersible polymers, e.g. polyether siloxanes, such as Tegopren® (Goldschmidt) or Belsil® (Wacker).

The polymers according to the invention can be used as a mixture with an amide-containing hair polymer. These include, for example, the polyurethanes described in DE-A-42 25 045, the above-described vinylpyrrolidone/acrylate terpolymers and acrylic acid/ethyl acrylate/N-tert-butylacrylamide terpolymers (e.g. Ultrahold®strong from BASF AG), the above-described amide-containing amphoteric polymers (e.g. Amphomer®) and in particular copolymers which have a proportion of amide-containing monomers, such as N-vinyllactams, of at least 30% by weight (e.g. Luviskol®plus and Luviskol®VA37 from BASF AG).

The other hair polymers are preferably present in amounts up to 10% by weight, based on the total weight of the composition.

A preferred hair-treatment composition comprises:
a) from 0.5 to 20% by weight, preferably from 1 to 10% by weight, of at least one water-soluble or -dispersible polymeric salt according to the invention,
b) from 50 to 99.5% by weight, preferably from 55 to 99% by weight, of a solvent chosen from water and water-miscible solvents, preferably $C_2$–$C_5$-alcohols, in particular ethanol, and mixtures thereof,
c) from 0 to 70% by weight, preferably from 0.1 to 50% by weight, of a propellant, preferably chosen from dimethyl ether and alkanes, such as, for example, propane/butane mixtures,
d) from 0 to 10% by weight, preferably from 0.1 to 10% by weight, of at least one water-soluble or -dispersible hair polymer which is different from a),
e) from 0 to 0.5% by weight, preferably from 0.001 to 2% by weight, of at least one water-soluble or water-dispersible silicone compound,
and customary additives.

The composition according to the invention can comprise, as component d), at least one other water-soluble or -dispersible hair polymer. The proportion of this component is then generally from about 0.1 to 10% by weight, based on the total weight of the composition. Preference is given in this connection to using water-soluble or water-dispersible polyurethanes which contain siloxane groups in copolymerized form.

The composition according to the invention can comprise, as component e), at least one nonionic, siloxane-containing, water-soluble or water-dispersible polymer, chosen in particular from the above-described polyether siloxanes. The proportion of this component is then generally from about 0.001 to 2% by weight, based on the total weight of the composition.

The composition according to the invention can comprise, as additional component, at least one water-insoluble silicone, in particular a polydimethylsiloxane, e.g. the Abil® grades from Goldschmidt. The proportion of this component is then generally from about 0.0001 to 0.2% by weight, preferably from 0.001 to 0.1% by weight, based on the total weight of the composition.

The composition according to the invention can additionally comprise, where appropriate, an antifoam based, for example, on silicone. The amount of the antifoam is then generally up to about 0.001% by weight, based on the total amount of the composition.

In addition to the abovementioned components, the composition according to the invention preferably comprises:
f) from 0 to 40% by weight, preferably from 0.1 to 35% by weight, of at least one surfactant,
g) from 0 to 5% by weight, preferably from 0.05 to 4% by weight, of at least one dye and/or UV absorber,
h) from 0 to 3% by weight, preferably from 0.05 to 2.5% by weight, of at least one salt,
i) from 0 to 3% by weight, preferably from 0.05 to 2.5% by weight, of at least one thickener,
and optionally other customary additives. These are then each generally present in an amount of from about 0 to 0.2% by weight, preferably from 0.001 to 0.2% by weight based on the total weight of the composition.

The compositions according to the invention have the advantage that on the one hand they impart the desired hold to hair and the polymers can be washed out easily (are redispersible), and on the other hand the hair remains elastic.

Advantageously, the salts according to the invention are also suitable as components in hair-treatment compositions which additionally comprise at least one other traditional hair polymer. With these mixtures, too, better flexibilities are generally achieved than for the corresponding polymers or mixtures which do not contain the salts according to the invention. The salts according to the invention are therefore also suitable for improving the elasticity of conventional hair-setting compositions. These then generally impart very good flexibility and suppleness to the hair.

The invention is illustrated in more detail by reference to the nonlimiting examples below.

EXAMPLES

The performance properties were assessed by the awarding of grades by independent experts. The properties tested and the grading scale are given in Table 1. To assess elasticity, tensile strength and feel, 20% strength by weight ethanolic solutions of the polymeric salts were in each case knife-coated as 500 μm films on polyethylene sheets and dried. To assess tackiness, wash-off and clarity, 5% strength by weight ethanolic solutions were in each case applied to a glass plate and dried.

TABLE 1

| | Grade | | | |
|---|---|---|---|---|
| | 1 | 2 | 3 | 4 |
| Elasticity | very soft | moderately soft | hard | brittle |
| Tensile strength | strong | moderately strong | poor | yielding |
| Feel | supple-smooth | moderately smooth | inhibiting | rough inhibiting |
| Tackiness | non-tacky | satisfactory | slightly tacky | tacky |
| Wash-off | very readily soluble | satisfactory | poorly soluble | insoluble |
| Clarity | clear | satisfactory | cloudy | milky, cloudy |

Polymer P1
Preparation of a Polyurethane with Free Carboxylic Acids

In a stirred apparatus equipped with stirrer, dropping funnel, thermometer, reflux condenser and equipment for working under nitrogen 1000 g (1 mol) of a polyester diol ($M_n$=1000 g/mol, prepared from isophthalic acid, adipic acid and 1,6-hexanediol), 124.8 g (1.2 mol) of neopentylglycol, 361.8 g (2.7 mol) of dimethylolpropanoic acid and 0.5 g of tetrabutyl orthotitanate were dissolved in 350 g of methyl ethyl ketone with heating to a temperature of about 50° C. and with stirring. 1111 g (5 mol) of isophorone diisocyanate were then added dropwise with stirring, and the reaction temperature increased. The reaction mixture was then stirred under reflux until the isocyanate group content of the mixture remained virtually constant, and then the mixture was cooled to room temperature with stirring. 13.4 g (0.1 mol) of 2-amino-2-methyl-1-propanol in the form of an aqueous solution with a temperature of about 40° C. were then added to the mixture to react the free isocyanate groups. Finally, the resulting polyurethane was then neutralized with 2.7 mol of an amine mixture of 2-amino-2-methyl-1-propanol and an amine according to Table 2 to 100%. The quantitative ratio of 2-amino-2-methyl-1-propanol to amine was then chosen such that the quantitative ratios of polyurethane to amine given in Table 4 were attained. The performance properties of the resulting polymeric salts are likewise given in Table 4. Distilling off the solvent under reduced pressure at 40° C. gives an aqueous (micro) dispersion. Pulverulent products can be obtained by spray drying.

Polymer P2
Preparation of a Polyacrylate Having Free Carboxylic Acid Groups 32.0 g of Feed 1 and 10.0 g of Feed 2 were introduced into a stirred apparatus fitted with reflux condenser, 4 separate feed devices and equipment for working under nitrogen, and the mixture was heated to 80° C. Following initial polymerization, recognizable when the viscosity starts to increase, the remainder of Feed 1 was added over the course of 3 hours and the remainder of Feed 2 was added over the course of 4 hours, the internal temperature being maintained at about 80° C. The mixture was then left to post-polymerize at this temperature for 2 hours. Feed 3 was then added over the course of 1 hour, the internal temperature being further maintained at 80° C. At the end of the addition, the mixture was post-polymerized at this temperature for a further 5 hours. After cooling, the reaction mixture was diluted with Feed 4. Finally, the resulting polymer was then neutralized to 100% with 0.85 mol of an amine mixture comprising 2-amino-2-methyl-1-propanol and an amine according to Table 2. Here, the quantitative ratio of 2-amino-2-methyl-1-propanol to amine was chosen such that the quantitative ratios of polymer to amine given in Table 4 were 5 attained. The performance properties of the resulting polymeric salts are likewise given in Table 4.

| Feed 1: | n-butylacrylate | 120.0 g |
|---|---|---|
|  | tert-butylacrylate | 105.0 g |
|  | methacrylic acid | 75.0 g |
| Feed 2: | ethanol | 100.0 g |
|  | tert-butyl perpivalate | 0.9 g |
| Feed 3: | ethanol | 150.0 g |
|  | tert-butyl perpivalate | 1.6 g |
| Feed 4: | ethanol | 200.0 g |

Polymer P3
Preparation of a Polyurethane Having Free Amino Groups

In a stirred apparatus fitted with stirrer, dropping funnel, thermometer, reflux condenser and equipment for working under nitrogen, 500 g (0.5 mol) of a polytetrahydrofuran (Mn=1000 g/mol), 124.8 g (1.2 mol) of neopentylglycol, 381.3 g (3.1 mol) of N-methyldiethanolamine and 0.3 g of tetrabutyl orthotitanate were dissolved in 350 g of methyl ethyl ketone with heating to a temperature of about 50° C. and with stirring. 1111 g (5 mol) of isophorone diisocyanate were then added dropwise with stirring, and the reaction temperature increased. The reaction mixture was then stirred under reflux until the isocyanate group content of the mixture remained virtually constant, and then the mixture was cooled to room temperature with stirring. Then, for the reaction of the free isocyanate groups, 40.2 g (0.3 mol) of 2-amino-2-methyl-1-propanol in the form of an aqueous solution was added to the mixture at a temperature of about 40° C. Finally, the resulting polyurethane was then neutralized to 100% with 2.7 mol of an acid mixture comprising lactic acid and an acid according to Table 3. Here, the quantitative ratio of lactic acid to acid according to Table 3 was chosen such that the quantitative ratios of polyurethane to amine given in Table 4 were attained. The performance properties of the resulting polymeric salts are likewise given in Table 4. The solvent was distilled off under reduced pressure at 40° C. to give an aqueous (micro)dispersion. Pulverulent products can be obtained by spray drying.

TABLE 2
Polyfunctional amines used for the neutralization of the polymers

| Amine | |
|---|---|
| A1 | N-Methyldipropylenetriamine |
| A2 | n-Tallow-propylenediamine (7 EO-units)[1] |
| A3 | Diaminopolyether/ethoxylated oleylamine (2 EO units)[2], molar ratio 1:1 |
| A4 | Pyrrolidone-containing polyamide (Itaconic acid: hexamethylenediamine, molar ratio 5:6) |
| A5 | Diaminopolyether siloxane[3] |

[1]Dinoramox ® S7, Ceca
[2]Noramox ® 02, Ceca
[3]Silsoft ® A-843, Witco

TABLE 3
Polybasic acids used for the neutralization of the polymers

| Acid | |
|---|---|
| S1 | Pyrrolidone-containing polyamide (Itaconic acid:hexamethylenediamine, molar ratio 6:5) |
| S2 | $H_3PO_4$ |

TABLE 4

| Ex. No. | Polymer:Poly-amine weight ratio | Elasticity | Tensile strength | Feel | Tackiness | Wash-off | Clarity |
|---|---|---|---|---|---|---|---|
| V1 | polyurethane P1 neutralized with AMP[4] | 3 | 2 | 2 | 1–2 | 1–2 | 1 |
| V2 | anionic polyacrylate P2 neutralized with AMP | 2–3 | 2–3 | 2 | 3 | 1 | 1 |
| V3 | cationic polyurethane P3 neutralized with MIS[5] | 2–3 | 2 | 2 | 3 | 1 | 1 |
| 1 | P1:A1 95:5 | 1 | 2 | 2 | 1–2 | 2 | 1–2 |
| 2 | P1:A2 95:5 | 2–3 | 1–2 | 1–2 | 1–2 | 1–2 | 1 |
| 3 | P1:A2 90:10 | 1–2 | 2 | 1–2 | 2 | 1 | 1 |
| 4 | P1:A2 80:20 | 1 | 3–4 | 2 | 3 | 1 | 1 |
| 5 | P1:A3 90:10 | 2 | 2–3 | 2 | 2 | 1 | 1 |
| 6 | P1:A4 90:10 | 2 | 2 | 2 | 2 | 1–2 | 1–2 |
| 7 | P1:A5 90:10 | 1–2 | 2–3 | 1 | 1–2 | 1–2 | 1–2 |
| 8 | P2:A1 90:10 | 1–2 | 2 | 2 | 3 | 1 | 1 |
| 9 | P2:A2 90:10 | 2 | 3 | 1–2 | 2 | 1 | 1 |
| 10 | P2:A3 90:10 | 2–3 | 3 | 1–2 | 2 | 1–2 | 1 |
| 11 | P2:A4 90:10 | 2 | 2 | 2–3 | 2–3 | 1 | 2 |
| 12 | P2:A5 90:10 | 1–2 | 3 | 1 | 2 | 1 | 1 |
| 13 | P3:S1 90:10 | 2 | 2 | 2 | 3 | 1–2 | 1–2 |
| 14 | P3:S2 95:5 | 2 | 1–2 | 1–2 | 2–3 | 2 | 1 |

Application Examples

Examples 15 to 28

Aerosol hairspray formulations with a VOC content of 97% by weight:

| | |
|---|---|
| Polymeric salt according to Ex. 1–14 | 3.00% by weight |
| Ethanol | 57.00% by weight |
| Dimethylether | 34.96% by weight |
| Perfume, additives | q.s. |

Examples 29 to 42

Compact aerosol hairspray formulations with a VOC content of 80% by weight:

| | |
|---|---|
| Polymeric salt according to Ex. 1–14 | 5.00% by weight |
| Ethanol | 40.00% by weight |
| Dimethylether | 34.96% by weight |
| Water | 15.00% by weight |
| Perfume, additives | q.s. |

Examples 43 to 56

Hairspray formulations with a VOC content of 55% by weight:

| | |
|---|---|
| Polymeric salt according to Ex. 1–14 | 3.00% by weight |
| Ethanol | 20.00% by weight |
| Water | 42.00% by weight |
| Dimethylether | 34.96% by weight |
| Perfume, additives | q.s. |

Examples 57 to 70

Pump hairspray:

| | |
|---|---|
| Polyurethane according to Ex. 1–14 | 5.00% by weight |
| Ethanol | 54.96% by weight |
| Water | 40.00% by weight |
| Perfume, additives | q.s. |

Examples 71 to 84

| Foam conditioner: | [% by wt] |
|---|---|
| Polymer 1-14 (25% strength aqueous solution) | 20.00 |
| Cremophor ® A25[4] | 0.20 |
| Comperlan ® KD[5] | 0.10 |
| Water | 69.70 |
| Propane/butane | 9.96 |
| Perfume, preservative | q.s. |

[4]CTFA-Name: Ceteareth 25, BASF AG, Reaction product of fatty alcohol and ethylene oxide
[5]CTFA-Name: Cocamide DEA, Henkel, coconut fatty acid amide To prepare the foam conditioner, the components are weighed in and dissolved with stirring. They are then transferred to a dispenser and the propellant is added.

Examples 85 to 98

| Conditioner shampoo: | | [% by wt] |
|---|---|---|
| A) | Texapon ® NSO 28% strength[6] | 50.00 |
| | Comperlan ® KD | 1.00 |
| | Polymer 1-14 (25% strength aqueous solution) | 20.00 |
| | Perfume oil | q.s. |
| B) | Water | 27.5 |
| | Sodium chloride | 1.5 |
| | Preservative | q.s. |

[6]Sodium lauryl sulfate; Henkel

To prepare the conditioner shampoos, the components A) and B) are separately weighed in and dissolved with mixing. Phase B) is then slowly added to phase A) with stirring.

Examples of Applications in Skin Cosmetics

Examples 99 to 112

O/W creams

| | % by weight | CTFA Name: |
|---|---|---|
| Oil phase: | | |
| Cremophor ® A6 (BASF AG) | 3.5 | Ceteareth-6 (stearyl alcohol ethoxylate) |
| Cremophor ® A25 (BASF AG) | 3.5 | Ceteareth-25 (fatty alcohol ethoxylate) |
| Glycerol monostearate s.e. | 2.5 | Glyceryl stearate |
| Paraffin oil | 7.5 | |
| Cetyl alcohol | 2.5 | |
| Luvitol ® EHO (BASF AG) | 3.2 | Cetearyl octanoate |
| Vitamin E acetate | 1.0 | Tocopheryl acetate |
| Nip-Nip ®, Nipa Laboratories Ltd., USA | 0.1 | Methyl and propyl 4-hydroxybenzoates (7:3) |
| Water phase: | | |
| Polymer 1-14 | 1.5 | |
| Water | 73.6 | |
| 1,2-Propylene glycol | 1.0 | Propylene glycol |
| Germall II, Sutton Laboratories Inc., USA | 0.1 | Imidazolidinylurea |

To prepare the creams, the components for the oil and water phase re weighed separately and homogenized at 80° C. The water phase is hen slowly added to the oil phase with stirring. The mixture is hen left to cool to room temperature with stirring.

Examples 113 to 126

O/W lotions

| | % by weight | CTFA Name: |
|---|---|---|
| Oil phase: | | |
| Cremophor ® A6 (BASF AG) | 2.0 | Ceteareth-6 (stearyl alcohol ethoxylate) |
| Cremophor ® A25 (BASF AG) | 2.0 | Ceteareth-25 (Fatty alcohol ethoxylate) |
| Glycerol monostearate | 6.0 | Glyceryl stearate |
| Paraffin oil | 0.9 | Paraffin oil |

-continued

| | % by weight | CTFA Name: |
|---|---|---|
| Tegiloxan ® 100 | 0.1 | Dimethicones (polydimethyl siloxane) |
| Cetyl alcohol | 1.5 | Cetyl alcohol |
| Luvitol ® EHO (BASF AG) | 12.0 | Cetearyl octanoate |
| Vitamin E acetate | 0.4 | Tocopheryl acetate |
| Nip-Nip ®, Nipa Laboratories Ltd., USA | 0.1 | Methyl and propyl 4-hydroxybenzoates (7:3) |
| Water phase: | | |
| Polymer 1-14 | 0.5 | |
| Water | 73.4 | |
| 1,2-Propylene glycol | 1.0 | Propylene glycol |
| Germall II, Sutton Laboratories Inc., USA | 0.1 | Imidazolidinylurea |

To prepare the O/W lotions, the components for the oil and water phase are separately weighed and homogenized at 80° C. The water phase is then slowly added to the oil phase with stirring. The mixture is then left to cool to room temperature with stirring.

We claim:

1. A water soluble or water-dispersible polymeric salt of:
   A) at least one polymer PA) having free acid groups and a neutralizing agent which comprises at least one compound VA) having at least two free amino groups per molecule, or
   B) at least one polymer PB) having free amino groups and a neutralizing agent which comprises at least one di- or polyvalent inorganic acid and/or at least one compound VB) having at least two free acid groups per molecule, where compounds VA) and VB) additionally have at least one hydrophilic group, which is chosen from other ionogenic and/or ionic groups, divalent radicals of polyethers, divalent radicals of pyrrolidone-containing polymers and combinations thereof,
where the component PA) or PB) comprises at least one pyrrolidone-containing polymer obtained by reacting monomeric mixture which comprises
   h) itaconic acid and/or a derivative thereof, and
   i) at least one diamine of the formula I $$H_2N-A-NHR^1 \quad (I)$$

in which
   $R^1$ is hydrogen or $C_1$–$C_4$-alkyl,
   A is a $C_2$–$C_{20}$-alkylene radical, which can be interrupted by at least one or more nonadjacent, identical or different —$NR^2$- groups, where $R^2$ is hydrogen, $C_1$–$C_4$-alkyl, $C_5$–$C_8$-cycloalkyl, phenyl or phenyl-$C_1$–$C_4$-alkyl.

2. A polymeric salt as claimed in claim 1, where the component VA) comprises at least one polyamine of the formula II $$HR^3N-R^5-(N-R^7)_p-NHR^4 \quad (II)$$
$$\qquad\qquad\; |$$
$$\qquad\qquad R^6$$

in which
   p is an integer from 0 to 4,
   $R^3$ and $R^4$ independently of one another are hydrogen, $C_1$- to $C_{40}$-alkyl or $C_6$- to $C_{40}$-alkenyl, where the alkyl and alkenyl radicals can carry at least one ionogenic and/or ionic group which is chosen from —COOY, —$SO_3$Y and —$PO_3$Y, where Y is H, Li, Na, K or ammonium, where, if p=0, at least one of the radicals $R^3$ or $R^4$ is a $C_1$- to $C_{40}$-alkyl or $C_6$- to $C_{40}$-alkenyl radical which carries at least one ionogenic and/or ionic group $R^5$ and $R^7$ are a $C_2$- to $C_6$-alkylene radical, where, if p is >1, the radicals $R^7$ are chosen independently from $C_2$- to $C_6$-alkylene radicals, $R^6$ is $C_1$- to $C_6$-alkyl, $C_5$- to $C_8$-cycloalkyl, phenyl or phenyl-$C_1$–$C_4$-alkyl, where, if p is >1, the radicals $R^6$ are chosen independently from these meanings.

3. A polymeric salt as claimed in claim 1, where the component VA) comprises at least one diaminopolyether of the formula III $$HR^8N-R^1-O-(CH_2CH_2O)_q(C_3H_6O)_r-R^{11}-NHR^9 \quad (III)$$

in which $R^8$ and $R^9$ independently of one another are hydrogen, $C_1$- to $C_{40}$-alkyl or $C_6$- to $C_{40}$-alkenyl, where the alkyl and alkenyl radicals may or may not carry at least one ionogenic and/or ionic group, which is chosen from —COOY, —$SO_3$Y and —$PO_3$Y, where Y is H, Li, Na, K or ammonium, $R^{10}$ and $R^{11}$ independently of one another are a $C_2$- to $C_6$-alkylene radical, the order of the alkylene oxide units is arbitrary, and q and r independently of one another are an integer from 0 to 100, where the sum q+r is in a range from 5 to 100.

4. A polymeric salt as claimed in claim 1, where the component VA) comprises at least one alkoxylated amine of the formula IV $$R^{12}R^{14}N-R^{16}-NR^{13}R^{15} \quad (IV)$$

in which $R^{12}$ and $R^{13}$, independently of one another are $C_1$- to $C_{40}$-alkyl, $C_6$- to $C_{40}$-alkenyl, hydroxy alkyl or a radical of the formula —$(CH_2CH_2O)_m(C_3H_6O)_n$—H, where the order of the alkylene units is arbitrary, and m and n independently of one another are an integer from 0 to 30, where the sum m+n is in a range from 1 to 30, $R^{14}$ and $R^{15}$ independently of one another are chosen from the meanings given for $R^{12}$ and $R^{13}$ and $C_2$- to $C_6$-alkyl radicals having an ionogenic or ionic group, which is chosen from —COOY, —$SO_3$Y and —$PO_3$Y, where Y is H, Li, Na, K or ammonium, and $R^{16}$ is a $C_2$- to $C_6$-alkylene radical.

5. A polymeric salt as claimed in claim 1, where the component VA) comprises at least one diaminopolyether siloxane of the formula V, which is chosen from polysiloxanes having repeat units of the formula V.1

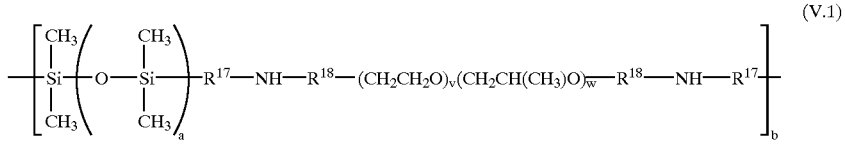

in which,
a is an integer from 0 to 100,
b is an integer from 1 to 8,
$R^{17}$ and $R^{18}$ independently of one another are $C_1$- to $C_8$-alkylene, the order of the alkylene oxides units is arbitrary and
v and w independently of one another are an integer from 0 to 200, where the sum of v+w is >0, polysiloxanes of the formula V.2

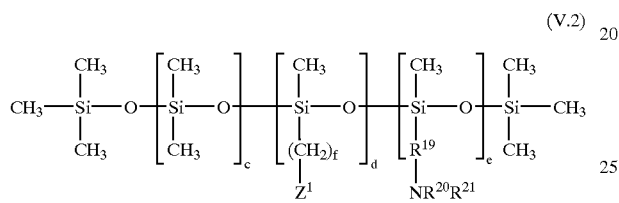

in which
$R^{19}$ is a $C_1$- to $C_8$-alkylene radical,
$R^{20}$ and $R^{21}$ independently of one another are hydrogen, $C_1$- to $C_8$-alkyl or $C_5$- to $C_8$-cycloalkyl,
the order of the siloxane units is arbitrary, c, d and e independently of one another are 0 to 100, where the sum c+d+e is at least 3,
f is an integer from 2 to 8,
$Z^1$ is a radical of the formula VI $$-R^{22}-(CH_2CH_2O)_g(CH_2CH(CH_3)O)_h-R^{23} \quad (VI)$$

in which
the order of the alkylene oxide units is arbitrary and
g and h independently of one another are an integer from 0 to 200, where the sum g+h is >0,
$R^{22}$ is a $C_1$- to $C_8$-alkylene radical, and
$R^{23}$ is hydrogen or a $C_1$- to $C_8$-alkyl radical, and mixtures thereof.

6. A polymeric salt as claimed in claim 1, where the component VA) comprises at least one pyrrolidone-containing polymer having at least two free primary, secondary and/or tertiary amino groups per molecule, or where the component VB) comprises at least one pyrrolidone-containing polymer having at least two free carboxylic acid groups per molecule.

7. A polymeric salt as claimed in claim 1, where the component PA) or PB) comprises at least one polyurethane which comprises, in incorporated form,
a) at least one polymer having at least two active hydrogen atoms per molecule,
b) at least one compound which has two active hydrogen atoms and at least one ionogenic and/or ionic group per molecule,
c) optionally at least one compound having a molecular weight in the range from 56 to 500, which contains two active hydrogen atoms per molecule, and
d) at least one diisocyanate.

8. A polymeric salt as claimed in claim 1, where the component PA) comprises at least one polymer which comprises, in copolymerized form,
e) at least one α,β-ethylenically unsaturated mono- and/or dicarboxylic acid,
f) at least one α,β-ethylenically unsaturated monomer, which is chosen from esters of α,β-ethylenically unsaturated mono- and/or dicarboxylic acids with straight-chain and/or branched $C_1$–$C_6$-alkanols, amides of α,β-ethylenically unsaturated mono- and/or dicarboxylic acids with mono- and dialkylamines having straight-chain and/or branched $C_1$–$C_6$-alkyl radicals and mixtures thereof,
g) optionally at least one other monomer, different from e) and f), having at least one α,β-ethylenically unsaturated double bond.

9. A polymeric salt as claimed in claim 1, where the ratio of A) free acid groups in the polymer PA) to free amino groups in the compound VA), or B) free amino groups in the polymer PB) to free acid groups in the compound VB) is in a range from 1:0.005 to 1:1.

10. A polymeric salt as claimed in claim 1, where the ratio of A) free acid groups in the polymer PA) to free amino groups in the compound VA), or B) free amino groups in the polymer PB) to free acid groups in the compound VB) is in a range from 1:0.01 to 1:0.5.

11. A cosmetic composition or pharmaceutical composition which comprises at least one polymeric salt as claimed in claim 1.

12. A cosmetic composition as claimed in claim 11 in the form of a hair-treatment composition, comprising
a) from 0.5 to 20% by weight of at least one polymeric salt, as defined in claim 1,
b) from 50 to 99.5% by weight of at least one solvent, chosen from water, water-miscible solvents and mixtures thereof,
c) from 0 to 70% by weight, of a propellant,
d) from 0 to 10% by weight of a water-soluble or -dispersible hair polymer different from a),
e) from 0 to 0.5% by weight of a water-soluble or water-dispersible silicone compound.

13. A cosmetic composition as claimed in claim 12, wherein component c) is from 1 to 50% by weight, of a propellant.

* * * * *